(12) United States Patent
Zergiebel et al.

(10) Patent No.: US 10,085,750 B2
(45) Date of Patent: Oct. 2, 2018

(54) ADAPTER WITH FIRE ROD J-HOOK LOCKOUT

(71) Applicant: Covidien LP, Mansfield, MA (US)

(72) Inventors: Earl Zergiebel, Guilford, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 479 days.

(21) Appl. No.: 14/811,428

(22) Filed: Jul. 28, 2015

(65) Prior Publication Data

US 2016/0113649 A1    Apr. 28, 2016

Related U.S. Application Data

(60) Provisional application No. 62/067,033, filed on Oct. 22, 2014.

(51) Int. Cl.
*A61B 17/04* (2006.01)
*A61B 17/10* (2006.01)
(Continued)

(52) U.S. Cl.
CPC ........ *A61B 17/07207* (2013.01); *A61B 19/30* (2013.01); *A61B 2017/0046* (2013.01); *A61B 2017/00398* (2013.01); *A61B 2017/00473* (2013.01); *A61B 2017/00477* (2013.01); *A61B 2017/00734* (2013.01)

(58) Field of Classification Search
CPC .. A61B 19/30; A61B 17/07207; A61B 17/072
USPC .......... 227/175.1–182.1; 606/139, 153–154, 606/219, 142–143
See application file for complete search history.

(56) References Cited

U.S. PATENT DOCUMENTS 2,777,340 A    1/1957    Hettwer et al.
2,957,353 A    10/1960    Babacz
(Continued)

FOREIGN PATENT DOCUMENTS

CA    2451558 A1    1/2003
CA    2824590 A1    4/2014
(Continued)

OTHER PUBLICATIONS

Extended European Search Report corresponding to International Application No. EP 15 15 1076.5 dated Apr. 22, 2015.
(Continued)

*Primary Examiner* — Robert Long

(57) ABSTRACT

A receiving assembly for releasably coupling a loading unit to an adapter while preventing inadvertent actuation of the loading unit includes a load link, a tip housing, and a locking member. The load link includes a distal portion and the tip housing defines a longitudinal slot and a lock opening. The locking member includes a member body and a locking tab extending from a lower surface thereof. The member body is disposed within the longitudinal slot of the tip housing. The locking member is moveable between an unlocked position such that the locking tab is positioned within the lock opening and a locked position such that the locking tab extends from the lock opening. The distal portion of the load link engages the member body of the locking member to pivot the locking member from the unlocked position to the locked position.

17 Claims, 11 Drawing Sheets

(51) Int. Cl.
*A61B 17/072* (2006.01)
*A61B 19/00* (2006.01)
*A61B 17/00* (2006.01)

(56) References Cited

U.S. PATENT DOCUMENTS

| | | | |
|---|---|---|---|
| 3,111,328 A | 11/1963 | Di Rito et al. | |
| 3,652,172 A * | 3/1972 | Zepell | B43K 24/04 |
| | | | 401/106 |
| 3,695,058 A | 10/1972 | Keith, Jr. | |
| 3,734,515 A | 5/1973 | Dudek | |
| 3,759,336 A | 9/1973 | Marcovitz et al. | |
| 4,158,974 A * | 6/1979 | Yamashita | B25B 13/52 |
| | | | 81/3.43 |
| 4,162,399 A | 7/1979 | Hudson | |
| 4,362,415 A * | 12/1982 | Metz | E02D 17/083 |
| | | | 248/285.1 |
| 4,606,343 A | 8/1986 | Conta et al. | |
| 4,660,717 A * | 4/1987 | Hofer | D01H 17/02 |
| | | | 206/338 |
| 4,697,482 A * | 10/1987 | Hutton | B25B 7/00 |
| | | | 24/20 EE |
| 4,705,038 A | 11/1987 | Sjostrom et al. | |
| 4,722,685 A | 2/1988 | de Estrada et al. | |
| 4,823,807 A | 4/1989 | Russell et al. | |
| 4,869,534 A * | 9/1989 | Ketcham | F16L 37/144 |
| | | | 285/24 |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,190,541 A | 3/1993 | Abele et al. | |
| 5,215,336 A * | 6/1993 | Worthing | F16L 19/005 |
| | | | 285/319 |
| 5,275,443 A * | 1/1994 | Klinger | F16L 37/144 |
| | | | 285/305 |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,405,175 A * | 4/1995 | Bonnah, II | F02M 55/004 |
| | | | 24/DIG. 53 |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,498,042 A * | 3/1996 | Dole | F16L 37/148 |
| | | | 285/148.27 |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,607,095 A | 3/1997 | Smith et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,669,918 A * | 9/1997 | Balazs | A61B 17/1155 |
| | | | 227/176.1 |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,848,455 A * | 12/1998 | Ikehara | A44B 19/306 |
| | | | 24/422 |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,343,772 B1 * | 2/2002 | Oi | F16L 33/03 |
| | | | 248/65 |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,539,920 B1 * | 4/2003 | Spiers | F02M 55/004 |
| | | | 123/456 |
| 6,610,066 B2 | 8/2003 | Dinger et al. | |
| 6,611,793 B1 | 8/2003 | Burnside et al. | |
| 6,612,622 B2 * | 9/2003 | Andre | F16L 33/00 |
| | | | 285/305 |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |

(56) References Cited

U.S. PATENT DOCUMENTS

| | | |
|---|---|---|
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,347,454 B2 * | 3/2008 | Martus ............ F16L 33/03 24/20 R |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,527,185 B2 * | 5/2009 | Harari ............ A61B 17/0643 227/179.1 |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,220,840 B2 * | 7/2012 | Garraffa ............ B63C 11/205 128/201.27 |
| 8,235,273 B2 | 8/2012 | Olson et al. |
| 8,241,322 B2 | 8/2012 | Whitman et al. |
| 8,272,554 B2 | 9/2012 | Whitman et al. |
| 8,276,594 B2 | 10/2012 | Shah |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |

(56) References Cited

U.S. PATENT DOCUMENTS

| | | | |
|---|---|---|---|
| 8,919,630 B2 | 12/2014 | Milliman | |
| 8,931,680 B2 | 1/2015 | Milliman | |
| 8,939,344 B2 | 1/2015 | Olson et al. | |
| 8,950,646 B2 | 2/2015 | Viola | |
| 8,960,519 B2 | 2/2015 | Whitman et al. | |
| 8,961,396 B2 | 2/2015 | Azarbarzin et al. | |
| 8,967,443 B2 | 3/2015 | McCuen | |
| 8,968,276 B2 | 3/2015 | Zemlok et al. | |
| 8,968,337 B2 | 3/2015 | Whitfield et al. | |
| 8,992,422 B2 | 3/2015 | Spivey et al. | |
| 9,009,927 B2* | 4/2015 | Rigollet | F16L 33/03 24/270 |
| 9,016,545 B2 | 4/2015 | Aranyi et al. | |
| 9,023,014 B2 | 5/2015 | Chowaniec et al. | |
| 9,033,868 B2 | 5/2015 | Whitman et al. | |
| 9,055,943 B2 | 6/2015 | Zemlok et al. | |
| 9,064,653 B2 | 6/2015 | Prest et al. | |
| 9,072,515 B2 | 7/2015 | Hall et al. | |
| 9,113,847 B2 | 8/2015 | Whitman et al. | |
| 9,113,875 B2 | 8/2015 | Viola et al. | |
| 9,113,876 B2 | 8/2015 | Zemlok et al. | |
| 9,113,899 B2 | 8/2015 | Garrison et al. | |
| 9,216,013 B2 | 12/2015 | Scirica et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 9,364,230 B2* | 6/2016 | Shelton, IV | A61B 17/07207 |
| 9,504,470 B2* | 11/2016 | Milliman | A61B 17/07292 |
| 9,506,592 B2* | 11/2016 | Turnau, III | F16L 37/0915 |
| 9,739,403 B2* | 8/2017 | Freter | F16L 37/0841 |
| 9,757,133 B2* | 9/2017 | Latimer | A61B 17/1155 |
| 9,845,907 B2* | 12/2017 | Hess | F16L 23/04 |
| 2001/0031975 A1 | 10/2001 | Whitman et al. | |
| 2002/0049454 A1 | 4/2002 | Whitman et al. | |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0111012 A1 | 6/2004 | Whitman | |
| 2004/0133189 A1 | 7/2004 | Sakurai | |
| 2004/0153124 A1 | 8/2004 | Whitman | |
| 2004/0176751 A1 | 9/2004 | Weitzner et al. | |
| 2004/0193146 A1 | 9/2004 | Lee et al. | |
| 2004/0194324 A1* | 10/2004 | Youn-Chyuan | B23D 51/10 30/337 |
| 2005/0085830 A1* | 4/2005 | Lehman | A61B 17/1285 606/143 |
| 2005/0099001 A1* | 5/2005 | Cassel | F01N 13/1805 285/23 |
| 2005/0125027 A1 | 6/2005 | Knodel et al. | |
| 2005/0131442 A1 | 6/2005 | Yachia et al. | |
| 2005/0192601 A1* | 9/2005 | Demarais | A61B 17/0401 606/151 |
| 2006/0142656 A1 | 6/2006 | Malackowski et al. | |
| 2006/0142740 A1 | 6/2006 | Sherman et al. | |
| 2006/0142744 A1 | 6/2006 | Boutoussov | |
| 2006/0259073 A1 | 11/2006 | Miyamoto et al. | |
| 2006/0278680 A1 | 12/2006 | Viola et al. | |
| 2006/0284730 A1 | 12/2006 | Schmid et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175947 A1 | 8/2007 | Ortiz et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0176416 A1* | 8/2007 | Swank | F01N 13/1816 285/226 |
| 2007/0270784 A1 | 11/2007 | Smith et al. | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0147089 A1 | 6/2008 | Loh et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0237296 A1 | 10/2008 | Boudreaux et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0012533 A1 | 1/2009 | Barbagli et al. | |
| 2009/0078336 A1* | 3/2009 | Baudoux | B60K 15/04 141/311 R |
| 2009/0090763 A1 | 4/2009 | Zemlok et al. | |
| 2009/0099876 A1 | 4/2009 | Whitman | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0209990 A1 | 8/2009 | Yates et al. | |
| 2009/0254094 A1 | 10/2009 | Knapp et al. | |
| 2009/0299141 A1 | 12/2009 | Downey et al. | |
| 2010/0023022 A1 | 1/2010 | Zeiner et al. | |
| 2010/0069942 A1 | 3/2010 | Shelton, IV | |
| 2010/0193568 A1 | 8/2010 | Scheib et al. | |
| 2010/0211053 A1 | 8/2010 | Ross | |
| 2010/0225073 A1 | 9/2010 | Porter et al. | |
| 2011/0071508 A1 | 3/2011 | Duval et al. | |
| 2011/0077673 A1 | 3/2011 | Grubac et al. | |
| 2011/0095070 A1* | 4/2011 | Patel | A61B 17/115 227/181.1 |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0142529 A1* | 6/2011 | Oh, II | A46B 7/04 401/268 |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1 | 7/2011 | Ross et al. | |
| 2011/0184245 A1 | 7/2011 | Xia et al. | |
| 2011/0204119 A1 | 8/2011 | McCuen | |
| 2011/0205072 A1* | 8/2011 | Ben-Mansour | G01M 3/183 340/605 |
| 2011/0218522 A1 | 9/2011 | Whitman | |
| 2011/0276057 A1 | 11/2011 | Conlon et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0211542 A1 | 8/2012 | Racenet | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0093149 A1 | 4/2013 | Saur et al. | |
| 2013/0123705 A1* | 5/2013 | Holm | A61M 25/0105 604/171 |
| 2013/0167365 A1* | 7/2013 | Herren | F16L 1/06 29/700 |
| 2013/0181035 A1 | 7/2013 | Milliman | |
| 2013/0184704 A1 | 7/2013 | Beardsley et al. | |

(56) References Cited

U.S. PATENT DOCUMENTS

| | | | |
|---|---|---|---|
| 2013/0200607 A1* | 8/2013 | Rodenberg | F16L 37/0915 |
| | | | 285/82 |
| 2013/0214025 A1 | 8/2013 | Zemlok et al. | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0001236 A1* | 1/2014 | Shelton, IV | A61B 17/07207 |
| | | | 227/176.1 |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0110455 A1 | 4/2014 | Ingmanson et al. | |
| 2014/0116832 A1* | 5/2014 | Beiser | F16D 41/14 |
| | | | 192/54.1 |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0217148 A1* | 8/2014 | Penna | A61B 17/07292 |
| | | | 227/179.1 |
| 2014/0236173 A1 | 8/2014 | Scirica et al. | |
| 2014/0236174 A1 | 8/2014 | Williams et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0365235 A1 | 12/2014 | DeBoer et al. | |
| 2014/0373652 A1* | 12/2014 | Zergiebel | F16H 19/02 |
| | | | 74/89.23 |
| 2015/0014392 A1 | 1/2015 | Williams et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0133957 A1 | 5/2015 | Kostrzewski | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2016/0157856 A1* | 6/2016 | Williams | A61B 17/068 |
| | | | 227/175.1 |
| 2016/0192934 A1* | 7/2016 | Williams | A61B 17/105 |
| | | | 227/176.1 |
| 2016/0279279 A1* | 9/2016 | Wonnacott | A61L 9/048 |
| 2017/0079660 A1* | 3/2017 | Sgroi | A61B 17/068 |

FOREIGN PATENT DOCUMENTS

| | | |
|---|---|---|
| CN | 102247182 A | 11/2011 |
| DE | 102008053842 A1 | 5/2010 |
| EP | 0705571 A1 | 4/1996 |
| EP | 1769754 A1 | 4/2007 |
| EP | 2055243 A2 | 5/2009 |
| EP | 2316345 A1 | 5/2011 |
| EP | 2333509 A1 | 6/2011 |
| EP | 2668910 A2 | 12/2013 |
| ES | 2333509 A1 | 2/2010 |
| JP | 08-038488 | 2/1996 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, dated Dec. 21, 2015.

Extended European Search Report corresponding to International Application No. EP 14 19 7563.1 dated Aug. 5, 2015.

Partial European Search Report corresponding to International Application No. EP 15 19 0643.5 dated Feb. 26, 2016.

Extended European Search Report corresponding to International Application No. EP 15 16 6899.3 dated Feb. 3, 2016.

Extended European Search Report corresponding to International Application No. EP 14 19 9783.3 dated Dec. 22, 2015.

Extended European Search Report corresponding to International Application No. EP 15 17 3807.7 dated Nov. 24, 2015.

Extended European Search Report corresponding to International Application No. EP 15 19 0760.7 dated Apr. 1, 2016.

Extended European Search Report corresponding to International Application No. EP 15 17 3803.6 dated Nov. 24, 2015.

Extended European Search Report corresponding to International Application No. EP 15 17 3804.4 dated Nov. 24, 2015.

Extended European Search Report corresponding to International Application No. EP 15 18 8539.9 dated Feb. 17, 2016.

Extended European Search Report corresponding to International Application No. EP 15 17 3910.9 dated Nov. 13, 2015.

European Office Action corresponding to International Application No. EP 14 15 2236.7 dated Aug. 11, 2015.

Extended European Search Report corresponding to International Application No. EP 15 18 4915.5 dated Jan. 5, 2016.

Extended European Search Report corresponding to counterpart International Application No. EP 14 18 4882.0 dated May 12, 2015.

Canadian Office Action corresponding to counterpart International Application No. CA 2640399 dated May 7, 2015.

Japanese Office Action corresponding to counterpart International Application No. JP 2011-197365 dated Mar. 23, 2015.

(56) References Cited

OTHER PUBLICATIONS

Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.

* cited by examiner

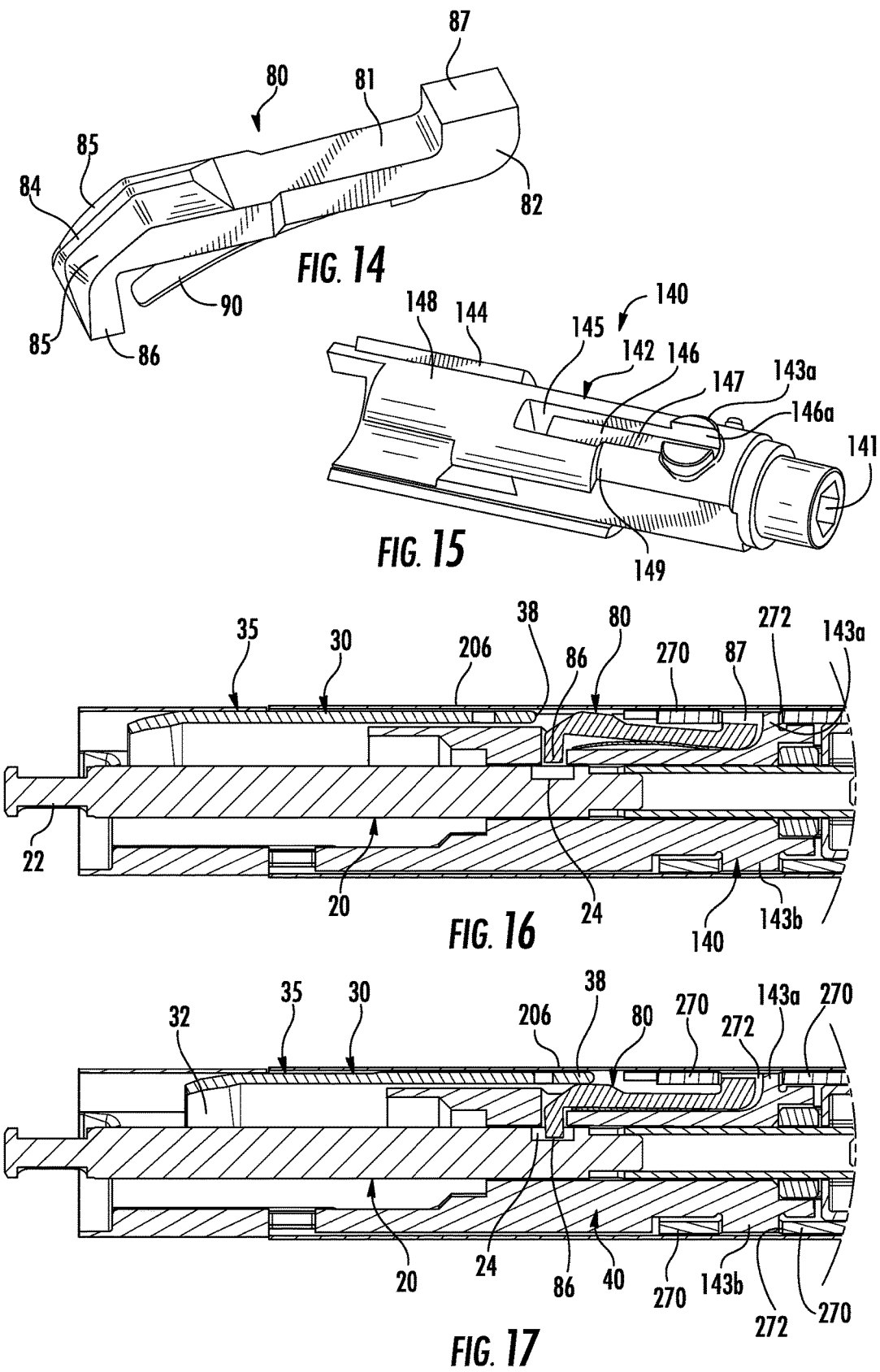

ADAPTER WITH FIRE ROD J-HOOK LOCKOUT

CROSS-REFERENCE TO RELATED APPLICATIONS

This application claims the benefit of and priority to U.S. Provisional Patent Application No. 62/067,033 filed Oct. 22, 2014, the entire disclosure of which is incorporated by reference herein.

BACKGROUND

1. Technical Field

The present disclosure relates to surgical instruments and, more specifically, to mechanical lockouts for surgical instruments.

2. Discussion of Related Art

A number of surgical device manufacturers have developed product lines with proprietary drive systems for operating and/or manipulating electromechanical surgical devices. In many instances, the electromechanical surgical devices include a reusable handle assembly, a reusable adapter assembly, and disposable or single use end effectors. The adapters are connected to the handle assembly prior to use and then disconnected from the handle assembly following use in order to be sterilized for re-use. In some instances, the adapters are integrally formed with the handle assembly and the end effectors are connected to the adapters prior to use and then disconnected from the adapters following use in order to be disposed of or in some instances sterilized for re-use.

Typically, the adapter or handle assembly includes drive structure which is coupled to a drive member in the end effector when the end effector is secured to the adapter or the handle assembly. To assure proper connection of the end effector to the adapter or handle assembly, the drive structure must be in a pre-fired refracted state.

As such, locking mechanisms that can prevent inadvertent movement of the drive structure of the adapter prior to securement of the adapter to the end effector to facilitate proper securement of the end effector to the adapter are beneficial.

SUMMARY

In an aspect of the present disclosure, a receiving assembly for releasably coupling a loading unit of an adapter of a surgical instrument includes a load link, a tip housing, and a locking member. The load link includes a link body having a distal portion. The tip housing includes a housing body that defines a longitudinal slot and a lock opening. The locking member includes a member body having upper and lower surfaces and a locking tab extending from the lower surface of the member body. The member body of the locking member is disposed within the longitudinal slot of the tip housing. The locking member is moveable between an unlocked position such that the locking tab is positioned within the lock opening and a locked position such that the locking tab extends through the lock opening. The distal portion of the load link is moveable into engagement with the member body of the locking member to pivot the locking member from the unlocked position to the locked position.

In aspects, the housing body of the tip housing defines a passage about the longitudinal axis of the tip housing such that in the locked position the locking tab extends into the passage. The assembly may include a biasing member positioned adjacent the lower surface of the locking member that urges the locking member towards the unlocked position.

In some aspects, the tip housing includes a coupling nub that protrudes from the housing body which is aligned with and is proximal to the lock opening. The longitudinal slot may extend into the coupling nub and the locking member may include a proximal locking tab. The proximal locking tab may extend from the upper surface of the member body and be positioned within the portion of the longitudinal slot that extends into the coupling nub.

In certain aspects, the member body defines a first body width along an axis that is transverse to a longitudinal axis of the tip housing. The locking tab may define a tab width along the transverse axis which is greater than the first body width. The body member may include proximal portion which defines the first body width and distal portion which defines a second body width that is greater than the first body width. The tab width may be greater than the second body width.

In particular aspects, the receiving assembly has a distal position in which the distal portion of the load link is proximal to the longitudinal slot and the lock opening of the tip housing and the locking member is in the unlocked position. The assembly may have a proximal position in which the distal portion of the load link is translated proximally to move the locking member to the locked position.

In another aspect of the present disclosure, an adaptor for releasably coupling a loading unit to a surgical instrument includes an outer tube, a coupling member, a control rod, a tip housing, a load link, and a locking member. The outer tube includes proximal and distal ends and defines a longitudinal axis therebetween. The coupling member defines a coupling opening adjacent a distal end thereof. The control rod is positioned along the longitudinal axis of the outer tube and defines a locking slot. The control rod is longitudinally translatable along the longitudinal axis between a retracted position and an advanced position. The tip housing includes a housing body that defines a passage which receives the control rod therethrough, a longitudinal slot, and a lock opening in communication with the passage and the longitudinal slot. The load link includes a link body having a distal portion. The link body defines a channel that receives the control rod. The link body is positioned distal to the housing body of the tip housing. The locking member includes a member body having upper and lower surfaces and a locking tab that extends from the lower surface of the member body. The member body of the locking member is disposed within the longitudinal slot of the tip housing. The locking member is moveable between an unlocked position in which the locking tab is positioned outside of the locking slot of the control rod and a locked position in which the locking tab is positioned in the locking slot of the control rod to prevent longitudinal translation of the control rod. The distal portion of the load link is movable into engagement with the member body of the locking member to move the locking member from the unlocked position to the locked position.

In aspects, the housing body includes a coupling nub that protrudes from the upper surface adjacent a proximal end of the housing body. The coupling member may be received within the coupling opening of the coupling member to longitudinally fix the tip housing within the outer tube.

In some aspects, the load link has a distal position in which the distal portion is distal to the longitudinal slot and the lock opening of the tip housing and the locking member is in the unlocked position. In addition, the load link has a proximal position in which the distal portion is translated proximally to pivot the locking member to the locked position.

In some aspects the adaptor includes a drive shaft that is engaged with a proximal end of the control rod. The drive shaft may be supported about the longitudinal axis and may be translatable along the longitudinal axis through the channel of the load link and the passage of the tip housing. The proximal end of the control rod may be coupled to the drive shaft. When the load link is in the distal position, the drive shaft and the control rod extend distally such that the locking slot is offset from the lock opening. The load link may be prevented from transitioning from the distal position to the proximal position by the locking tab engaging the outer surface of one of the control rod or the drive shaft.

In certain aspects, the locking member includes a camming surface that extends from the upper surface of the tip housing adjacent a distal end of the locking member. The distal portion may engage the camming surface to pivot the locking member to the locked position. The camming surface may be in contact with the outer tube when the locking member is in the unlocked position.

In particular aspects, the longitudinal slot extends into the coupling tube and the locking member includes a proximal locking tab that extends from the upper surface of the member body. When the locking member is in a locked position, the proximal locking tab may engage the coupling opening of the coupling member to transmit a longitudinal force from the locking tab to the coupling member to prevent longitudinal translation of the control rod.

In another aspect of the present disclosure, a method of coupling a loading unit to an adaptor of a surgical instrument includes inserting a connector of a loading unit into a distal end of an outer tube of an adapter and rotating the loading unit relative to the outer tube. Inserting the connector of the loading unit into the distal end of the outer tube of the adapter includes the connector of the loading unit engaging a distal end portion of a load link to translate the load link to a proximal position. The distal end portion of the load link pivoting the locking member such that a locking tab of the locking member extends from a lock opening defined by a tab housing and into a locking slot formed in a control rod to prevent the control rod from translating longitudinally. Rotating the loading unit relative to the outer tube permits the load link to move distally to a distal position such that the locking member is pivotable out of the locking slot of the control rod to permit the control rod to translate longitudinally.

In aspects, the method includes applying a distal longitudinal force to the control rod when the load link is in the proximal position such that the locking tab of the locking member is within the locking slot of the control rod. The locking slot may engage the locking tab to prevent distal translation of the control rod when the distal longitudinal force is applied.

In some aspects, the method includes transferring the longitudinal force from the locking tab of the locking member to a coupling member of the adapter disposed over a coupling nub of the tip housing. The locking member may include a proximal locking tab that is disposed within a portion of the longitudinal slot defined by the coupling nub. The proximal locking tab may engage a coupling opening defined by the coupling member to transfer the longitudinal force to the coupling member.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 14 is a perspective view of still another exemplary embodiment of a locking member in accordance with the present disclosure;

FIG. 15 is a perspective view of another embodiment of a tip housing in accordance with the present disclosure;

FIG. 16 is a side cross-sectional view of a distal end of an adapter with the locking member of FIG. 14 positioned within the tip housing of FIG. 15 in an initial configuration; and FIG. 17 is a side cross-sectional view of the distal end of the adapter of FIG. 16 in a locked configuration.

DETAILED DESCRIPTION

Figure 1:
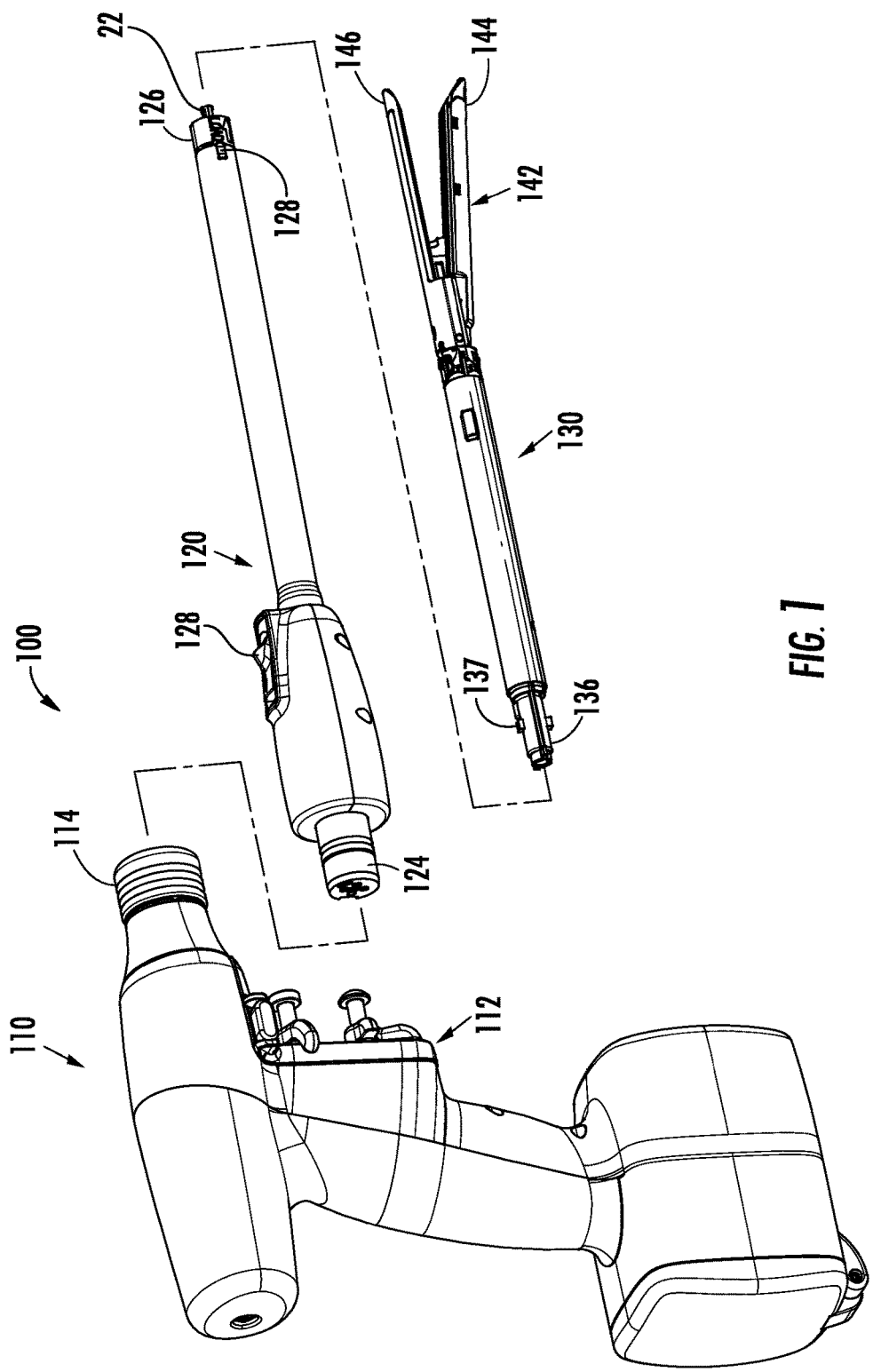
FIG. 1 is a perspective view of an exemplary embodiment of a surgical instrument in accordance with the present disclosure with parts separated.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 2:
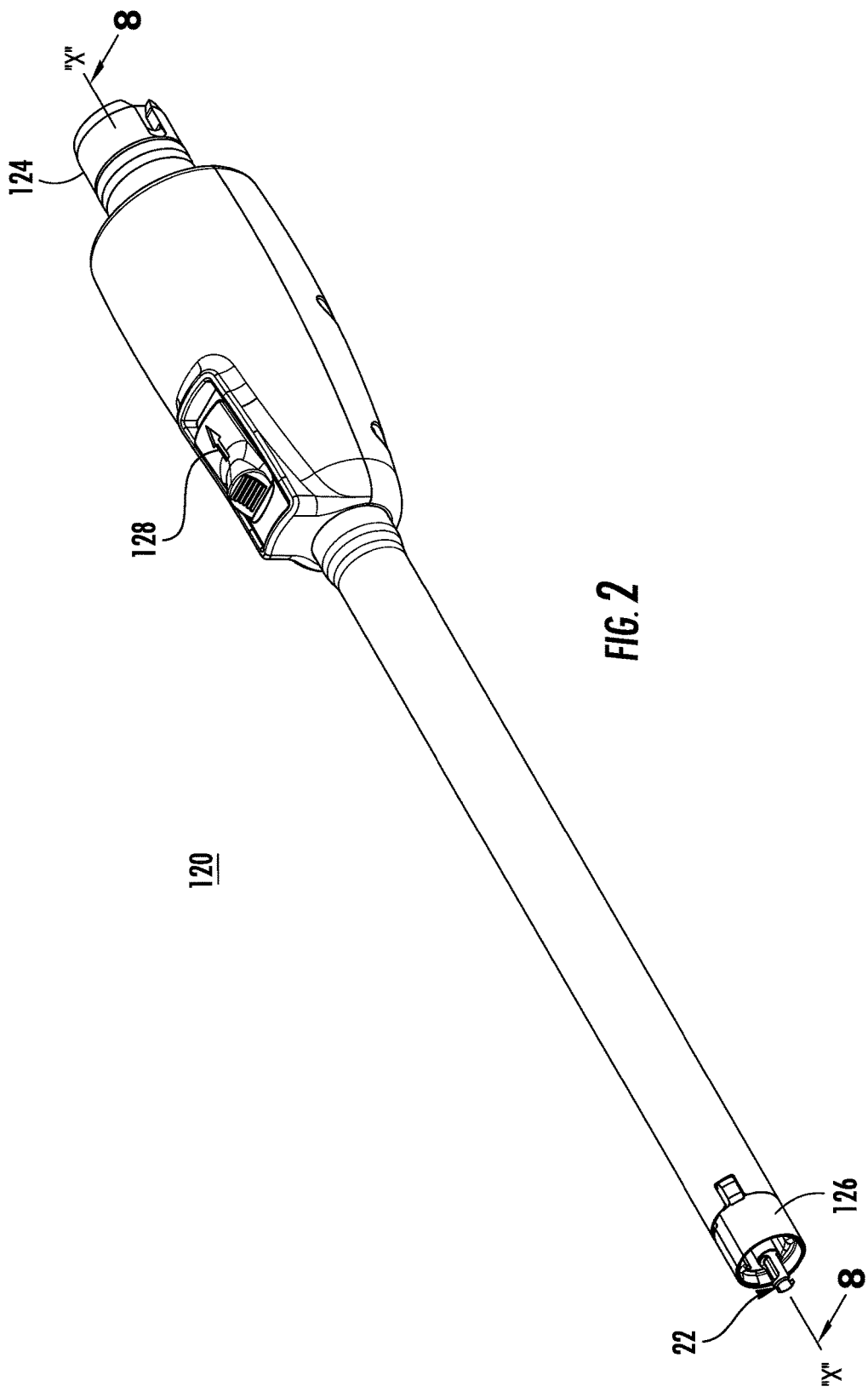
FIG. 2 is a perspective view of the adapter of the surgical instrument of FIG. 1.

Referring now to FIGS. 1 and 2, an exemplary embodiment of a surgical instrument 100 is provided in accordance with the present disclosure including a handle 110, an adapter 120, and a loading unit 130. The surgical instrument 100 is configured to capture tissue within the loading unit 130, act on the captured tissue (e.g., staple or suture the captured tissue), and sever the captured tissue. Exemplary surgical instruments and loading units are disclosed in commonly owned and co-pending U.S. patent application Ser. No. 13/331,047, filed Dec. 20, 2011, and published as U.S. Patent Publication No. 2012/0089131 on Apr. 12, 2012, and Ser. No. 13/484,975, filed May 31, 2012, and published as U.S. Patent Publication No. 2012/0253329 on Oct. 4, 2012 ("the '975 Application"). The content of each of these applications is incorporated herein by reference in its entirety.

The handle 110 is a powered handle and may include one or more drive shafts (not shown) that move (e.g., rotate) independently of one another. The handle 110 includes a control interface 112 and a receiver 114. The control interface 112 includes one or more control(s) associated with the drive members (not shown) on the handle 110 (e.g., an actuator switch or button, a clamp button, a firing button, etc.). The receiver 114 is supported at the distal end of the handle 110 and defines a recess configured to receive an interface (e.g., interface 124) of an adapter or, alternatively, of a loading unit (e.g., a connector 136). An exemplary powered handle is disclosed in the '975 Application, the contents of which were previously incorporated herein by reference in its entirety. It is also contemplated that the handle 110 may be a manually driven handle with one or more output shafts. Such a manually driven handle is disclosed, e.g., in U.S. Pat. No. 8,636,766, which is incorporated herein by reference in its entirety.

The loading unit 130 includes an end effector 142 having first and second jaw members 144, 146 for acting on tissue captured therebetween, and a connector 136 for releasably securing the loading unit 130 to the adapter 120, or in the alternative, directly to the handle 110. The adapter 120 includes a receiver assembly 126 for releasably securing the connector 136 of the loading unit 130 to the adapter 120.

Figure 3:
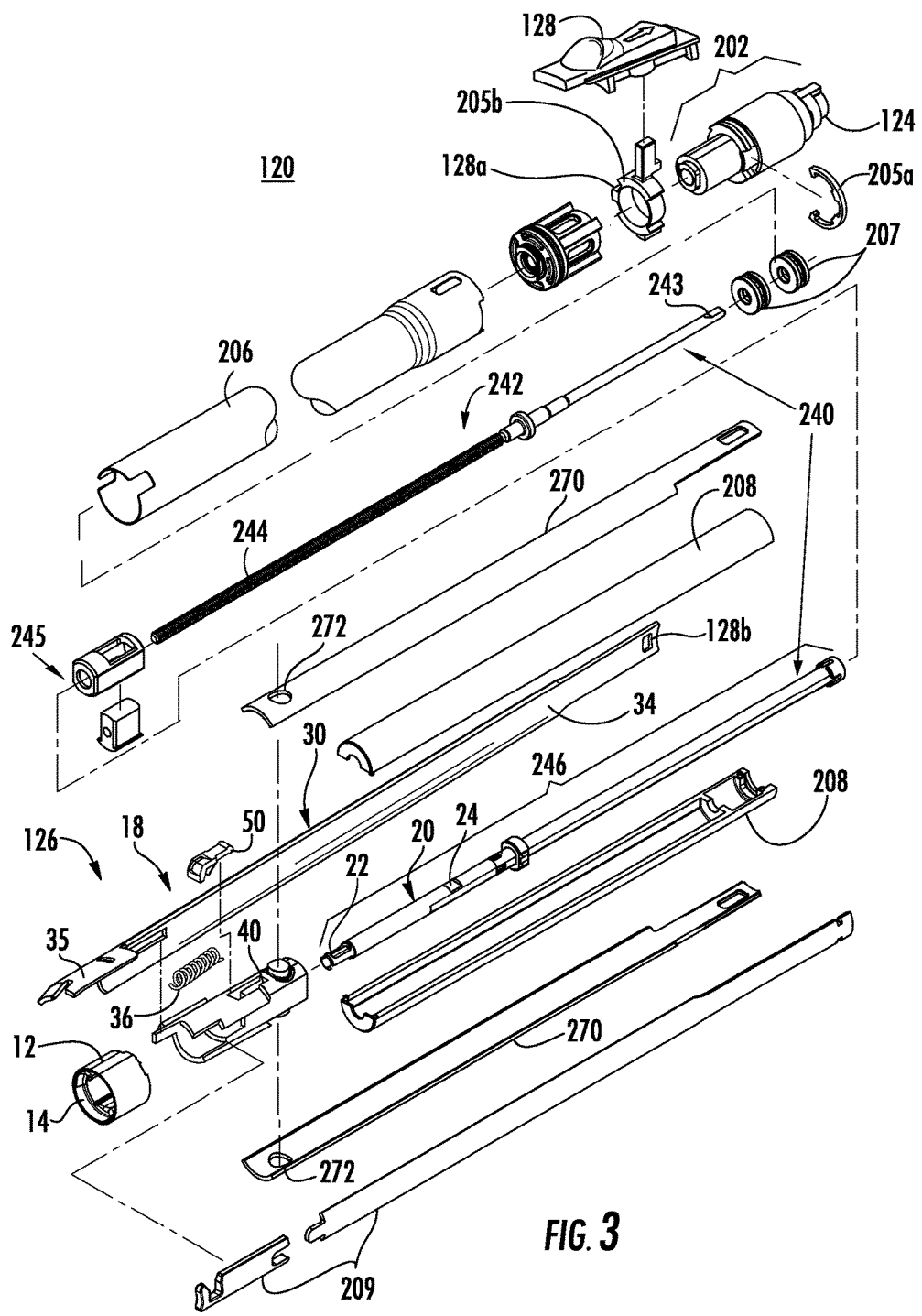
FIG. 3 is an exploded view showing the components of the adapter of FIG. 2.

Referring to FIG. 3, the adapter 120 includes a drive converting assembly 240 that converts the motion of the drive shaft(s) of the handle 110 (FIG. 1) into linear motion of a control rod 20. The drive converting assembly 240 includes a first drive shaft 242, a driven nut 245, and a second drive shaft 246. The first drive shaft 242 is rotatably supported within a housing 202 of the adapter 120 and an outer tube 206 which receives the housing 202. The proximal end 243 of the first drive shaft 242 is supported by the housing 202 and is operatively associated with the drive shaft(s) of the handle 110 (FIG. 1) such that when the adapter 120 is coupled to the handle 110, movement (e.g., rotation) of the drive shaft(s) (not shown) of the handle 110 effects movement (e.g., rotation) of the first drive shaft 242.

The first drive shaft 242 includes a distal threaded portion 244. The driven nut 245 is rotatably fixed within an inner tube 208 and is disposed on the threaded portion 244 of the first drive shaft 242. As such, as the first drive shaft 242 is rotated about the longitudinal axis thereof, the driven nut 245 is translated along the longitudinal axis of the first drive shaft 242 along the inner tube 208. The driven nut 245 is connected to the distal end of the second drive shaft 246 to longitudinally translate the second drive shaft 246 in response to the longitudinal translation of the driven nut 245.

The adapter 120 may include an articulation shaft 209 for articulating a portion of the loading unit 130 (e.g., the end effector 140) relative to the longitudinal axis of the adapter 120. A proximal end of the articulation shaft 209 is retained to the interface 124 by a retention ring 205a. A switch support 205b is positioned over a distal portion of the housing 202 and is configured to support a release switch 128. The switch support 205b receives bearings 207 which support the switch support 205b for longitudinal sliding movement along a proximal end of the first drive shaft 242. The internal components and operation of the drive converting assembly 240 are described in greater detail in the '975 Application, which is incorporated by reference herein.

With reference also to FIGS. 1 and 2, the control rod 20 (FIG. 3) includes a connector 22 that extends from the receiver assembly 126 of the adapter 120 (FIG. 2). The connector 136 (FIG. 1) of the loading unit 130 is inserted into the receiver assembly 126 of the adapter 120 to position the connector 22 (FIG. 2) of the adapter 120 within the connector 136 of the loading unit 130. The end effector 142 is actuated in response to the longitudinal translation of the control rod 20.

Figure 4:
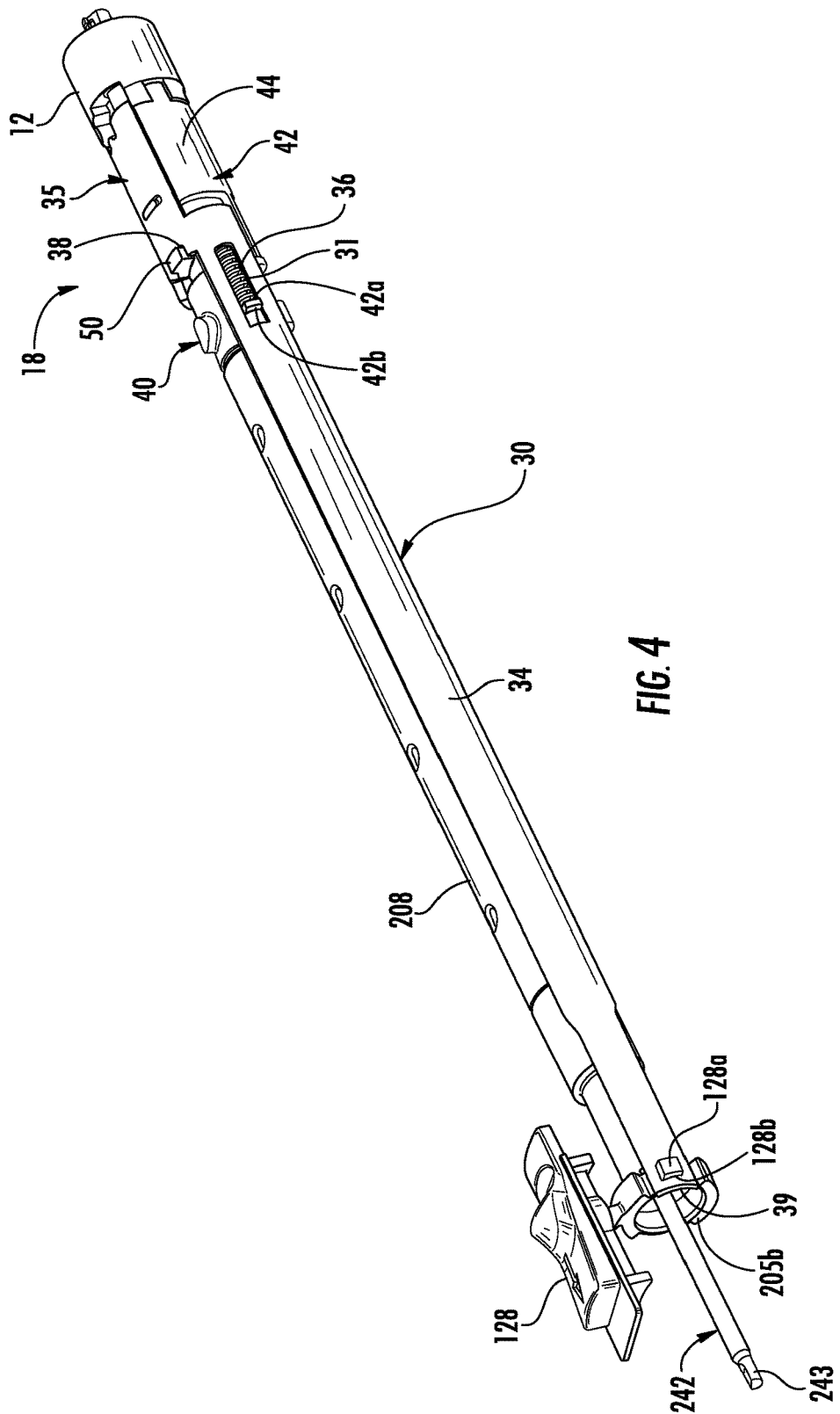
FIG. 4 is a rear perspective view of the adapter of FIG. 2 with the outer tube and proximal support removed.
Figure 5:
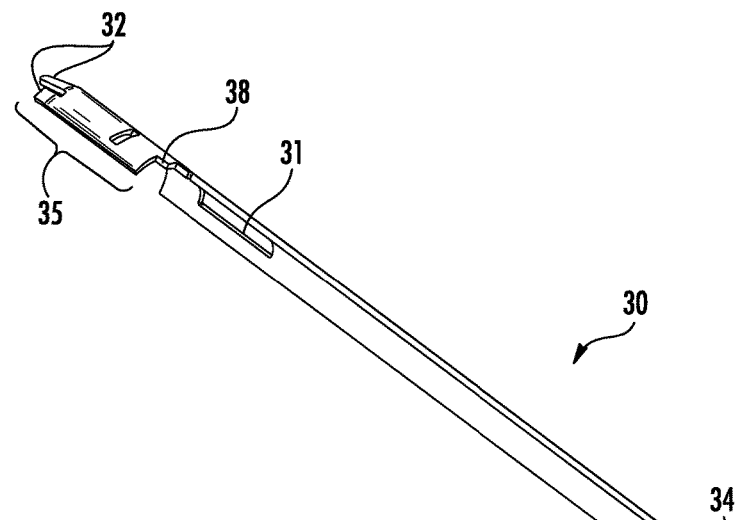
FIG. 5 is a perspective view of the load link of the adapter of FIG. 4.

Referring to FIGS. 3 and 4, the receiver assembly 126 is positioned at a distal end of the adapter 120 and includes a distal ring 12 defining a distal opening 14, and a locking mechanism 18. The adapter 120 includes coupling members 270 which extend within the outer tube 206 distally from the housing 202 (FIG. 3) to the receiver assembly 126. Each coupling member 270 defines a coupling opening 272 that is positioned adjacent to a distal end of the coupling member 270 and receives a portion of the receiver assembly 126 to support and longitudinally fix the receiver assembly 126 within the outer tube 206.

Referring to FIGS. 3-7, the locking mechanism 18 (FIG. 4) prevents coupling and decoupling of the loading unit 130 to the adapter 120 if the control rod 20 is improperly positioned within the adapter 120 as detailed below. In addition, the locking mechanism prevents longitudinal movement of the control rod 20 as the loading unit 130 is coupled to the adapter 120 to prevent inadvertent actuation of the end effector 140 adapter. Moreover, the locking mechanism 18 prevents actuation of the end effector 140 if the loading unit 130 is not properly or fully coupled to the adapter 120.

With particular reference to FIGS. 3 and 4, the locking mechanism 18 includes a load link 30, a tip housing 40, and a locking member 50. The load link 30 (FIG. 5) includes a body 34 that extends between the switch support 205b and the distal ring 12. The body 34 defines a support opening 128b adjacent a proximal end 39 thereof that receives a switch tab 128a of the switch support 205b to secure the load link 30 with the release switch 128. A distal portion 35 of the load link 30 is positioned adjacent an outer surface of the tip housing 40. The distal portion 35 of the body of the load link 30 includes engagement fingers 32 (FIG. 5) which are positioned to engage tabs 137 (FIG. 1) of the connector 136 of the loading unit 130 as the loading unit 130 is secured to the adapter 120. The load link 30 includes a camming recess 38 that extends proximally from the distal portion 35. The body 34 of the load link 30 defines a biasing slot 31 adjacent the tip housing 40 that is configured to receive a biasing member 36 to bias the load link 30 distally relative to the tip housing 40.

Figure 6:
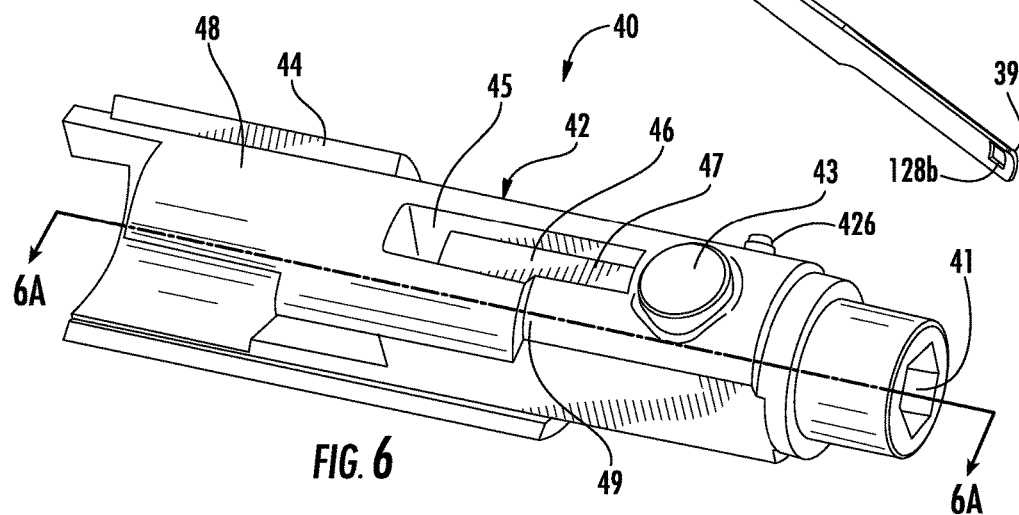
FIG. 6 is a perspective view of the tip housing of the adapter of FIG. 4.
Figure 6A:
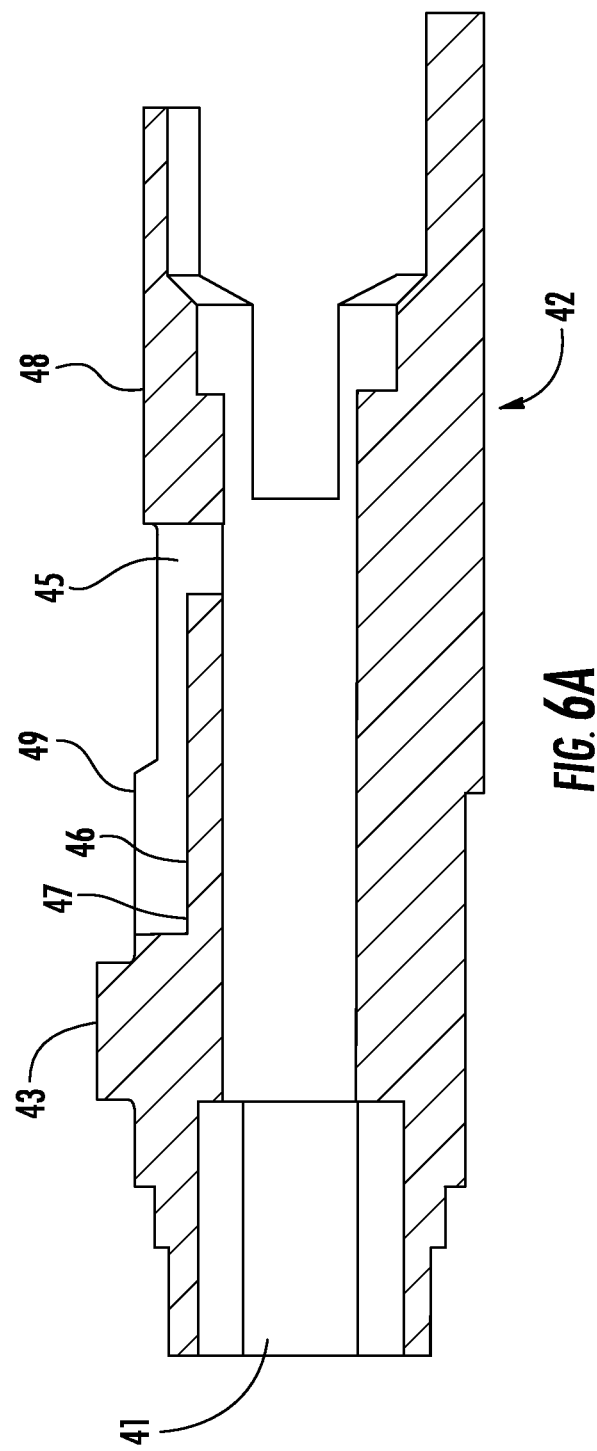
FIG. 6A is a cross-sectional view taken along the section line 6A-6A of FIG. 6.
Figure 9A:
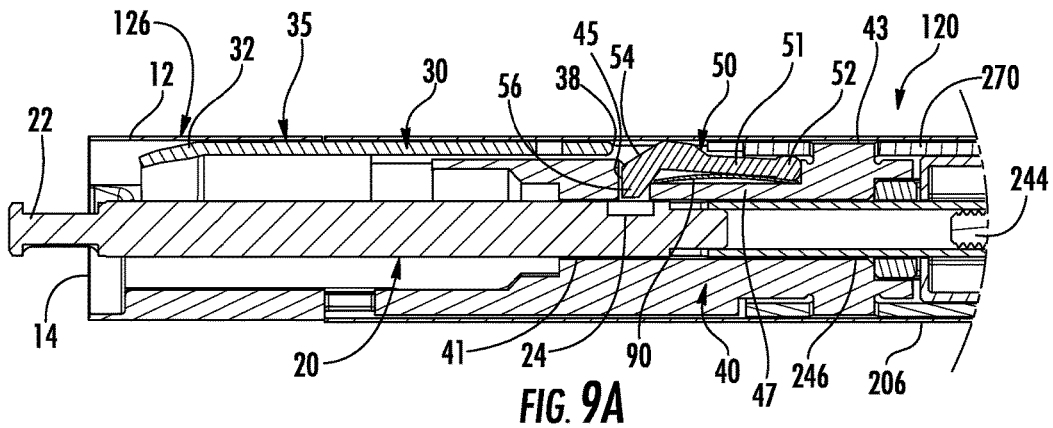
FIGS. 9A, 10A, and 11A are enlarged views of the area of detail of FIG. 8 as the locking mechanism transitions from an initial configuration to a locked configuration.
Figure 10A:
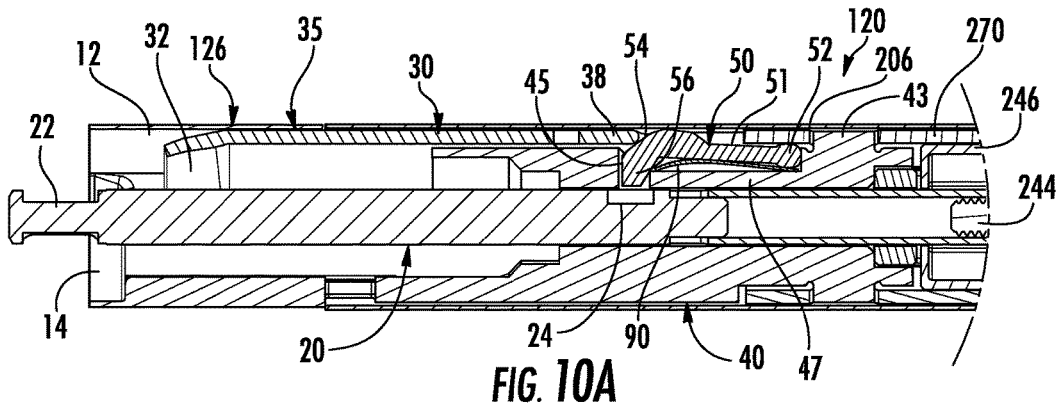

As best shown in FIGS. 6 and 6A, the tip housing 40 (FIG. 6) defines a passage 41 that slidably receives the control rod 20 (FIG. 9A). The passage 41 may also slidably receive portions of the second drive shaft 246 (FIG. 9A). The tip housing 40 includes a body 42 defining a biasing recess 42a (FIG. 4) which receives a portion of the biasing member 36. The body 42 may include a biasing tab 42b at a proximal end of the biasing recess 42a that is slidably received within the biasing channel 31 of the load link 30 to radially align the load link 30 relative to the tip housing 40. The body 42 defines a lock opening 45 that communicates with the passage 41 and a longitudinal slot 46 in an outer surface thereof. The lock opening 45 is positioned distally of and in communication with the longitudinal slot 46. The longitudinal slot 46 defines a ledge 47 that is positioned within the longitudinal slot 46 and below the outer surface of the body 42. The outer surface of the body 42 defines a race 48 positioned distal to and axially aligned with the lock opening 45.

The body 42 may include a distal shoulder 44 positioned adjacent one side of the distal portion 35 (FIG. 5) of the load link 30. The distal shoulder 44 is positioned to limit distal translation of the load link 30 relative to the tip housing 40 by the engagement of the body 34 of the load link 30 with the distal shoulder 44 of the tip housing 42. The distal shoulder 44 may also radially align the distal portion 35 of the load link 30 with the tip housing 40. The body 42 may also include a proximal shoulder 49 that is positioned adjacent the other side of the distal portion 35 of the load link 30 to radially align the distal portion 35 of the load link 30 with the tip housing 40.

Figure 7:
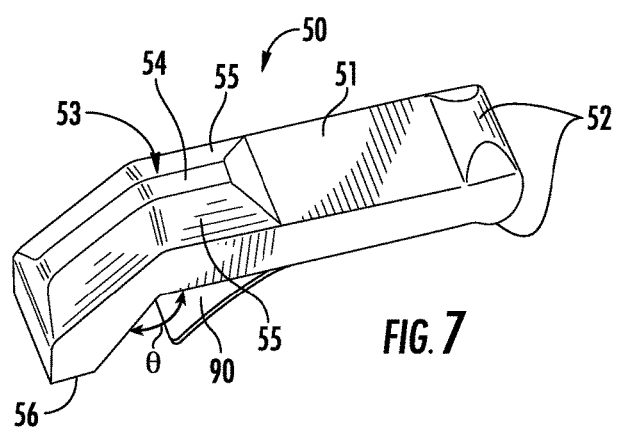
FIG. 7 is a perspective view of the locking member of the adapter of FIG. 4.

Referring to FIG. 7, the locking member 50 includes a body 51 and a locking tab 56 positioned at a distal end of the locking member 50. The body 51 is disposed within the longitudinal slot 46 of the tip housing 40. The proximal end of the locking member 50 includes nubs 52 which extend from upper and lower surfaces of the body 51 adjacent a proximal end thereof. The nubs 52 are positioned between a distal end of the coupling member 270 and the ledge 47 (FIG. 9A) of the tip housing 40 to pivotally support the locking member 50 within the slot 46. Alternatively, other components can be provided to pivotally support the locking member 50 within the longitudinal slot 46.

The locking tab 56 extends distally and downwardly from the body 51 to define an angle θ with the body 51 such that the locking tab 56 of the locking member 50 is disposed substantially within the lock opening 45. The angle θ may be in a range from about 91° to about 135° (e.g., 100°). The angle θ permits the control rod 20 to pivot the locking member 50 out of the locking slot 24 when the load link 30 is in a distal position as detailed below. The distal end of the locking member 50 includes a camming surface 53 which extends from the upper surface of the locking member 50 and includes a longitudinal camming portion 54 and radial camming portions 55.

In embodiments, the locking member 50 includes a biasing member 90 coupled to the proximal end of the locking member 50. The biasing member 90 is positioned between the lower surface of the locking member 50 and the ledge 47 (FIG. 6A) of the tip housing 40 to urge the locking tab 56 away from the control rod 20 and out of the locking slot 24 as shown in FIG. 9A.

Figure 8:
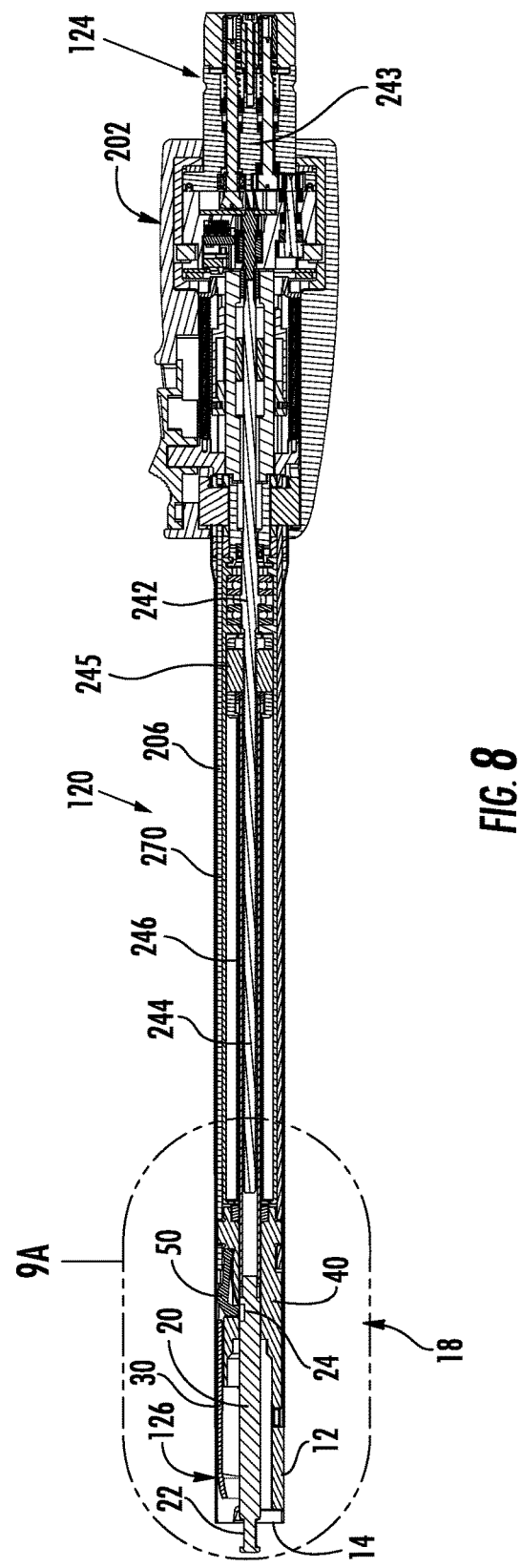
FIG. 8 is a side cross-sectional view taken along section line 8-8 of FIG. 2.
Figure 9B:
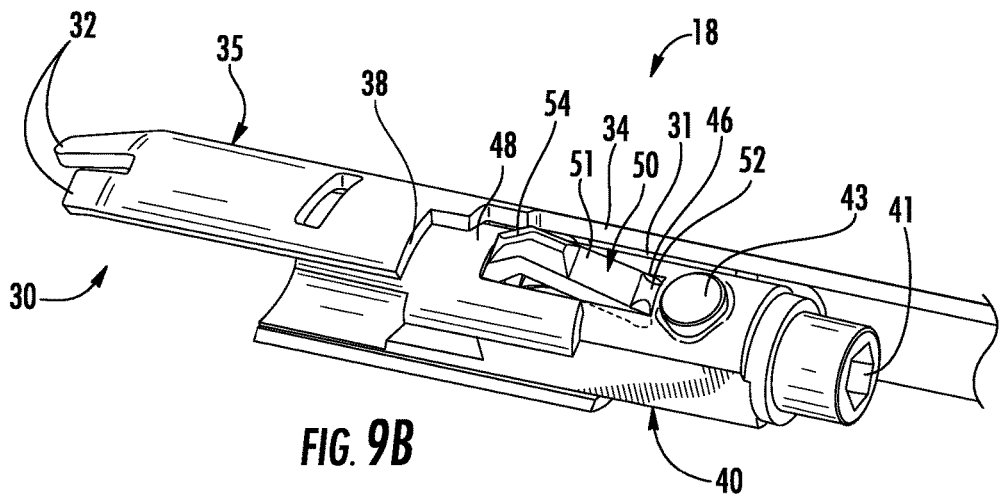
FIGS. 9B, 10B, and 11B are perspective views of the locking mechanism of FIG. 8 as the locking mechanism transitions from an initial configuration to a locked configuration.
Figure 10B:
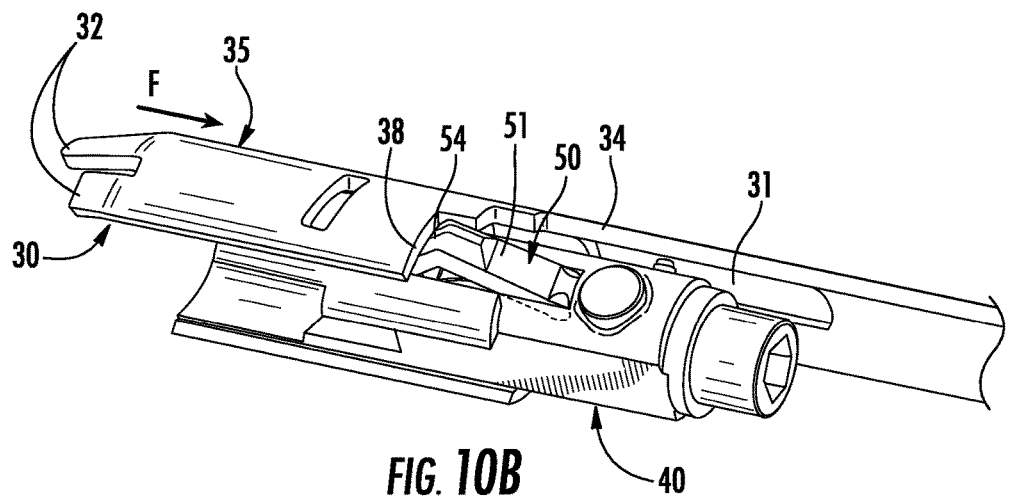

Referring to FIGS. 8, 9A, and 9B, prior to attachment of a loading unit 130 (FIG. 1) to the adapter 120, the locking mechanism 18 has an initial configuration in which the body 51 of the locking member 50 is positioned in the longitudinal slot 46 of the tip housing 40 with the locking tab 56 spaced radially outwardly of the control rod 20. The control rod 20 is positioned within the tip housing 40 such that the locking slot 24 of the control rod 20 is positioned beneath the lock opening 45 as illustrated in FIG. 9A. In embodiments including the biasing member 90, the biasing member 90 engages the ledge 47 within the slot 46 to urge the locking tab 56 upwardly within opening 45 away from the control rod 20 such that the control rod 20 is free to longitudinally translate within the tip housing 40. The distal portion 35 of the load link 30 is positioned distal to the lock opening 45 of the tip housing 40 such that the locking member 50 is free to pivot in and out of the lock opening 45.

Figure 11A:
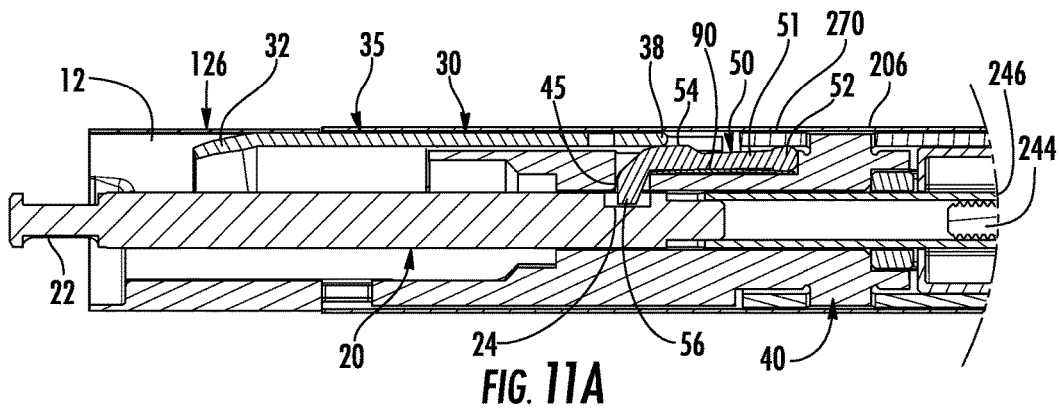
Figure 11B:
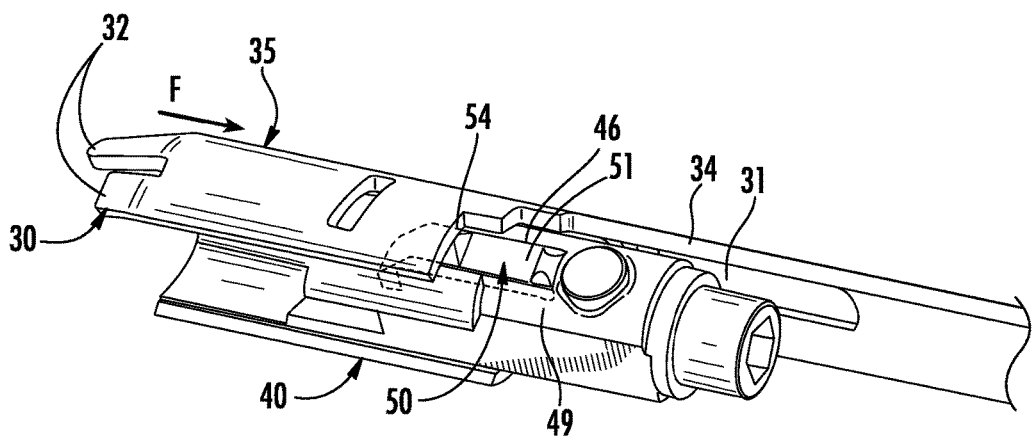

With reference to FIGS. 10A-11B, as the loading unit 130 is inserted into the receiving assembly 126 (FIG. 1), portions of the connector 136 of the loading unit 130 (e.g., engagement nubs 137) engage the engagement fingers 32 of the load link 30 to urge the load link 30 proximally into a proximal position such that the receiving assembly 126 of the adapter 120 is moved to a locked configuration (FIGS. 11A and 11B). More specifically, as the connector 136 of the loading unit 130 is inserted into the receiving assembly 126 of the adapter 120, the connector 136 pushes the distal portion 35 of the load link 30 proximally such that the distal portion 35 moves proximally to engage the longitudinal camming portion 54 of the locking member 50 positioned within the camming recess 38 to pivot the locking member 50 downwardly on the nub 52. As the locking member 50 pivots downwardly, the locking tab 56 moves through the lock opening 45 into the locking slot 24 of the control rod 20. When the locking tab 56 is positioned within the locking slot 24, the control rod 20 is prevented from longitudinal translation.

After the load link 30 is in the proximal position and the receiving assembly 126 is in the locked configuration, the loading unit 130 is rotated relative to the adapter 120 to a fully secured configuration secured to the adapter 120. It will be appreciated that the loading unit 130 is rotatably coupled to the adapter 120 via a bayonet type connection that couples the connector 22 of the control rod 20 within the connector 136 of the loading unit 130. Such a bayonet type coupling is disclosed in U.S. Pat. No. 5,782,396 which is incorporated herein by reference in its entirety.

When the loading unit 130 is rotated in relation to the adapter 120 to fully secure the loading unit 130 to the adapter 120, the portions of the connector 136 engaged with the engagement fingers 32 of the load link 30 are rotated out of engagement with the engagement fingers 32 to permit the load link 30 to be urged distally by the biasing member 36 (FIG. 4) to its home or distal position (FIGS. 9A, 9B). With the load link 30 in the distal position and the loading unit 130 fully secured to the adapter 120, the control rod 20 may be actuated to move distally through the passage 41 of the tip housing 40. As the control rod 20 moves distally with the load link 30 in its distal position, the walls of the locking slot 24 engage the J-shape of the locking tab 56 such that the control rod 20 pivots the locking tab 56 from within the locking slot 24. Additionally, or alternatively, in embodiments including the biasing member 90, the biasing member 90 may pivot the locking tab 56 out of the locking slot 24 when the load link 30 returns to its distal position.

It will be appreciated that if the locking slot 24 of the control rod 20 is not aligned with the lock opening 45 of the tip housing 40 that the locking member 50 will not be able to pivot downwardly to facilitate proximal movement of the load link 30. Thus, the locking assembly 18 will prevent the loading unit 130 from being coupled to the adapter 120. More specifically, when the loading unit 130 begins to move the load link 30 towards its proximal position, engagement of the locking tab 56 with the outer surface of the control rod 24 prevents the locking member 50 from pivoting downwardly in response to a wall defining the camming recess 38 of the body 34 of the load link 30 engaging the locking member 50. This engagement of the wall defining the camming recess 38 with the locking member 50 prevents the loading unit 130 from moving proximally to a position wherein the loading unit 130 is permitted to rotate to its fully secured configuration.

When the control rod 20 is advanced in the fully secured configuration of the loading unit 130, the locking slot 24 of the control rod 20 moves out of alignment with the lock opening 45 of the tip housing 40. As such, the load link 30 is prevented from moving towards its proximal position. More specifically, in the fully secured configuration, the locking member 50 is prevented from pivoting downward through the lock opening 45 as the distal portion 35 of the load link 30 moves proximally into engagement with the camming surface 54. This engagement prevents the load link 30 from moving towards its proximal position. In addition, when the load link 30 is in its distal position, the distal portion 35 of the load link 30 prevents the loading unit 130 from rotating from its fully secured position. More specifically, engagement of the nubs 137 (FIG. 1) of the connector 136 with the distal portion 35 of the load link 30 prevent rotation of the loading unit 30 in relation to the adapter 120.

The adapter 120 includes a release switch 128 (FIG. 1) to facilitate the release the loading unit 130 from the fully secured position. The release switch 128 is moveably supported adjacent a proximal end of the adapter 120 to selectively move the load link 30 towards its proximal position against the biasing member 36. More specifically, movement of the release switch 128 effects movement of the switch tab 128a. The switch tab 128 (FIG. 4) is positioned within the switch recess 128b (FIG. 4) such that movement of the switch tab 128a effects movement of the load link 30. As the load link 30 is moved towards its proximal position, the distal portion 35 engages the locking member 50 to pivot the locking tab 56 into the locking slot 24 of the control rod 20. It will be appreciated, that the load link 30 is prevented from moving to towards the proximal position when the locking slot 24 of the control rod 20 is not aligned with the locking slot 45. With the load link 30 in the proximal position, the loading unit 130 is permitted to rotate out of the fully secured position and to be withdrawn from the adapter 120.

Figure 12:
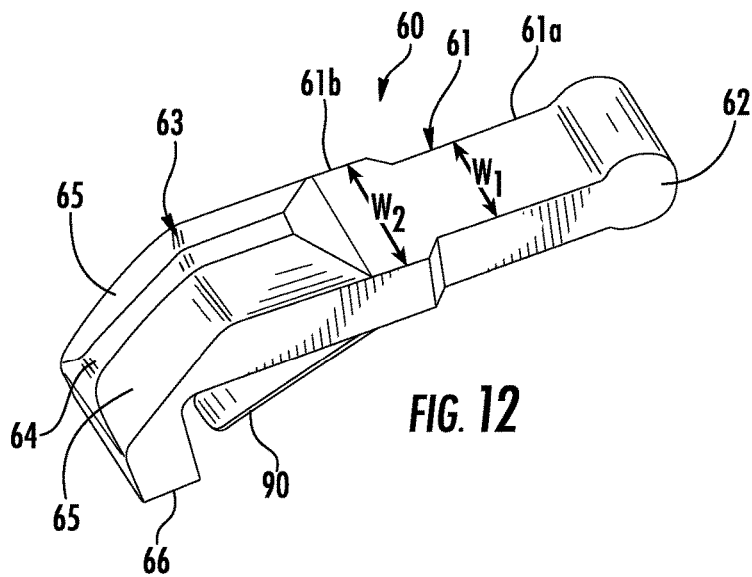
FIG. 12 is a perspective view of another exemplary embodiment of a locking member in accordance with the present disclosure.

Referring to FIG. 12, another locking member 60 is provided in accordance with the present disclosure. The locking member 60 is substantially similar to the locking member 50 detailed above. As such, only the differences will be detailed herein. The locking member 60 includes a body 61 having a proximal body portion 61a defining a first body width $W_1$ and a distal body portion 61b defining a second body width $W_2$ larger than the first body width $W_1$. The locking tab 66 has a width substantially equal to the second body width $W_2$ which is larger than the width of the locking tab 56 of the locking member 50. The larger width results in an increased cross-section of the locking tab 66 in engagement with the locking slot 24 of the control rod 20. The increased cross-section of engagement enables the locking tab 66 to prevent longitudinal translation of the control rod 20 in response to a greater longitudinal force applied to the control rod 20 as compared to the locking tab 56. It will be appreciated that the lock opening 45 and the longitudinal slot 46 of the tip housing 40 may be modified to receive the first and second body portions 61a, 61b of the locking member 60.

Figure 13:
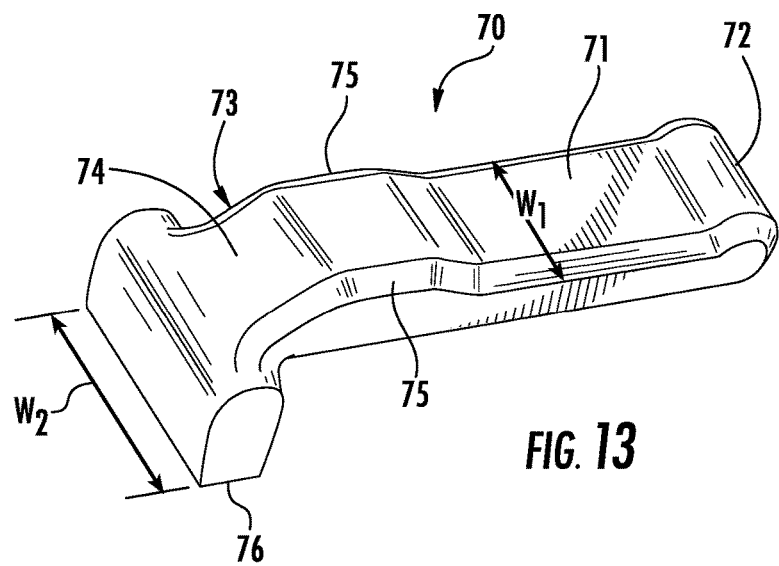
FIG. 13 is a perspective view of yet another exemplary embodiment of a locking member in accordance with the present disclosure.

Referring now to FIG. 13, yet another locking member 70 is provided in accordance with the present disclosure. The locking member 70 is substantially similar to the locking member 50 detailed above. As such, only the differences will be detailed herein. The locking member 70 includes a body 71 defining a body width $W_1$ and a locking tab 76 defining a tab width $W_2$ which is larger than the body width $W_1$. The larger width results in an increased cross-section of the locking tab 76 in engagement with the locking slot 24 of the control rod 20. The increased cross-section of engagement enables the locking tab 76 to prevent longitudinal translation of the control rod 20 in response to a greater longitudinal force applied to the control rod 20 when compared to the locking tab 56. It will be appreciated that by widening the locking tab 76, the body 71 may be disposed in the longitudinal slot 46 of the tip housing 40 without widening the longitudinal slot 46.

With reference to FIG. 14, still another locking member 80 is provided in accordance with the present disclosure. The locking member 80 is substantially similar to the locking member 60 detailed above. As such, only the differences will be detailed herein. The locking member 80 includes a body 81, a distal locking tab 86, and a proximal locking tab 87. The distal locking tab 86 is substantially similar to the locking tab 66 of the locking member 60 and will not be detailed herein. The proximal locking tab 87 extends from the upper surface of the body 81 at a distal end of the body 81.

With additional reference to FIG. 15, another tip housing 140 is provided in accordance with the present disclosure. The tip housing 140 is substantially similar to the tip housing 40 detailed above. As such, only the differences will be detailed herein. The tip housing 140 includes a body 142 having first and second coupling nubs 143a, 143b (FIG. 16). The first coupling nub 143a extends from the upper surface of the body 142 and the second coupling nub extends from the lower surface of the body 142. The body 142 defines a longitudinal slot 146 with a proximal portion 146a extending into the first coupling nub 143a.

Referring to FIG. 16, the locking member 80 has an unlocked position such that the distal locking tab 86 is positioned outside of the locking slot 24 of the control rod 20 permitting the control rod 20 to longitudinally translate relative to the outer tube 206. In the unlocked position, the proximal locking tab 87 is positioned outside (e.g., below) the coupling opening 272 of the coupling member 270.

Referring now to FIG. 17, the locking member 80 is engaged by the load link 30 to pivot the locking member 80 into a locked position such that the distal locking tab 86 is positioned within the locking slot 24 of the control rod 20 to prevent the control rod 20 from longitudinal translation relative to the outer tube 206. In the locked position, the proximal locking tab 87 is positioned within the coupling opening 272 of the coupling member 270 such that a longitudinal distal force applied to the distal locking tab 86 by the control rod 20 is transmitted directly to the coupling member 270 by the proximal locking tab 87 of the locking member 80 such that the longitudinal distal force is not transmitted to the tip housing 140.

In some embodiments, the coupling member 270 is constructed of a stronger material (e.g., steel) than the tip housing 140 (e.g., a plastic). Thus, transmitting the longitudinal distal force directly to the coupling member 270 may prevent damage to or extend the life of the tip housing 140. In addition, transmitting the longitudinal distal force directly to the coupling member 270 may permit the locking member 80 to prevent longitudinal translation of the control rod 20 in response to a greater longitudinal force applied to the control rod as compared to locking members 50, 60, and 70.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. A receiving assembly for releasably coupling a loading unit to an adapter of a surgical instrument, the receiving assembly comprising:
a load link including a link body having a distal portion;
a tip housing including a housing body defining a longitudinal slot and a lock opening; and
a locking member including a member body having an upper surface, a lower surface, and a locking tab, the member body of the locking member disposed within the longitudinal slot of the tip housing, the locking member being pivotable between an unlocked position, wherein the locking tab is positioned within the lock opening, and a locked position, wherein the locking tab extends through the lock opening, wherein the distal portion of the load link is moveable into engagement with the member body of the locking member to pivot the locking member from the unlocked position to the locked position.

2. The assembly of claim 1, wherein the housing body of the tip housing defines a passage about a longitudinal axis of the tip housing, and wherein in the locked position the locking tab extends into the passage.

3. The assembly of claim 1, wherein the tip housing includes a coupling nub protruding from the housing body aligned with and proximal to the lock opening.

4. A receiving assembly for releaseably coupling a loading unit to an adapter of a surgical instrument, the receiving assembly comprising:
a load link including a link body having a distal portion;
a tip housing including a housing body defining a longitudinal slot and a lock opening, the tip housing including a coupling nub protruding from the housing body aligned with and proximal to the lock opening; and
a locking member including a member body having an upper surface, a lower surface, and a locking tab, the member body of the locking member disposed within the longitudinal slot of the tip housing, the locking member being moveable between an unlocked position, wherein the locking tab is positioned within the lock opening, and a locked position, wherein the locking tab extends through the lock opening, wherein the distal portion of the load link is moveable into engagement with the member body of the locking member to pivot the locking member from the unlocked position to the locked position, the longitudinal slot extending into the coupling nub and the locking member including a proximal locking tab, the proximal locking tab extending from the upper surface of the member body and positioned within the coupling nub.

5. The assembly of claim 1, wherein the member body defines a first body width along an axis transverse to a longitudinal axis of the tip housing and the locking tab defines a tab width along the axis transverse to the longitudinal axis of the tip housing, the tab width being greater than the first body width.

6. The assembly of claim 5, wherein the member body has proximal and distal portions, the proximal portion defining the first body width, the distal portion defining a second body width along the axis transverse to the longitudinal axis of the tip housing, the second body width being greater than first body width.

7. The assembly of claim 6, wherein the tab width is greater than the second body width.

8. The assembly of claim 1, wherein the assembly has an distal position in which the distal portion of the load link is proximal to the longitudinal slot and the lock opening of the tip housing and the locking member is in the unlocked position, a proximal position in which the distal portion of the load link is translated proximally to move the locking member to the locked position.

9. The assembly of claim 1, further comprising a biasing member positioned adjacent the lower surface of the locking member to urge the locking member towards the unlocked position.

10. An adapter for releasably coupling a loading unit to a surgical instrument, the adapter comprising:
an outer tube having proximal and distal ends and defining a longitudinal axis;
a coupling member defining a coupling opening adjacent a distal end thereof;
a control rod positioned along the longitudinal axis of the outer tube and defining a locking slot, the control rod being longitudinally translatable along the longitudinal axis between a retracted position and an advanced position;
a tip housing including a housing body defining a passage, a longitudinal slot, and a lock opening in communication with the passage and the longitudinal slot, the passage receiving the control rod;
a load link including a link body having a distal portion; and
a locking member including a member body having an upper surface, a lower surface, and a locking tab extending from the lower surface of the member body, the member body of the locking member disposed within the longitudinal slot of the tip housing, the locking member being moveable between an unlocked position in which the locking tab is positioned outside of the locking slot of the control rod and a locked position in which the locking tab is positioned in the locking slot of the control rod to prevent longitudinal translation of the control rod, the distal portion of the load link being moveable into engagement with the member body of the locking member to move the locking member from the unlocked position to the locked position.

11. The adapter of claim 10, wherein the housing body includes a coupling nub protruding from the upper surface adjacent a proximal end of the housing body, the coupling nub received within the coupling opening of the coupling member to longitudinally fix the tip housing within the outer tube.

12. The adapter of claim 10, wherein the load link has a distal position in which the distal portion is distal to the longitudinal slot and lock opening of the tip housing and the locking member is in the unlocked position, and a proximal position in which the distal portion is translated proximally to pivot the locking member to the locked position.

13. The adapter of claim 12, further comprising a drive shaft engaged with a proximal end of the control rod, the drive shaft supported about the longitudinal axis and translatable along the longitudinal axis through the channel of the load link and the passage of the tip housing, the proximal end of the control rod coupled to the drive shaft.

14. The adapter of claim 13, wherein when the load link is in the distal position, the drive shaft and the control rod are extended distally such that the locking slot is offset from the lock opening, the load link prevented from transitioning from the distal position to the proximal position by the locking tab engaging the outer surface of one of the control rod or the drive shaft.

15. The adapter of claim 10, wherein the locking member includes a camming surface extending from the upper surface adjacent a distal end thereof, the distal portion engaging the camming surface to pivot the locking member to the locked position, the camming surface in contact with the outer tube when the locking member is in the unlocked position.

16. The adapter of claim 10, wherein the longitudinal slot extends into the coupling nub and the locking member includes a proximal locking tab, the proximal locking tab extending from the upper surface of the member body and positioned within the coupling nub.

17. The adapter of claim 16, wherein when the locking member is in the locked position, the proximal locking tab engages the coupling opening of the coupling member to transmit a longitudinal force from the locking tab to the coupling member to prevent longitudinal translation of the control rod.

* * * * *